US005780033A

United States Patent [19]

Torchilin et al.

[11] Patent Number: 5,780,033

[45] Date of Patent: Jul. 14, 1998

[54] USE OF AUTOANTIBODIES FOR TUMOR THERAPY AND PROPHYLAXIS

[76] Inventors: Vladimir P. Torchilin, 12 Shipway Pl., Charlestown, Mass. 02129; Leonid Z. Iakoubov, 51 Parker Terrace, Newton, Mass. 02159

[21] Appl. No.: 563,901

[22] Filed: Nov. 22, 1995

Related U.S. Application Data

[63] Continuation of Ser. No. 265,411, Jun. 24, 1994, abandoned.

[51] Int. Cl.[6] ...................... A61K 39/395; G01N 33/574; C12N 5/20; C07K 16/30

[52] U.S. Cl. .................................... 424/183.1; 424/138.1; 424/155.1; 424/174.1; 435/7.23; 435/70.21; 435/172.2; 435/344; 530/388.8; 530/389.7

[58] Field of Search .............................. 424/136.1, 138.1, 424/155.1, 178.1, 174.1, 183.1; 435/91, 70.21, 330, 7.23, 172.2, 344; 530/387.1, 388.21, 388.8, 389.7

[56] References Cited

FOREIGN PATENT DOCUMENTS 8705031 8/1987 WIPO .
WO 87/05031 8/1987 WIPO .

OTHER PUBLICATIONS

Ben–Yehuda et al., "Immune Senescence:Mechanisms and Clinical Implications", *Cancer Investigation*, 10(6):525–531 (1992).

Chen et al., "A Comparative Autoradiographic Study Demonstrationg Differential Intratumor Localization of Monoclonal Antibodies to Cell Surface (Lym–1) and Intracellular . . . ", *J. Nuc. Med.*, 31:1059–1066 (1990).

Jacob et al., "A monoclonal anti–double–stranded DNA autoantibody binds to a 94–kDa cell–surface protein on various cell types via nucleosomes or a DNA–histone complex", *Proc. Natl. Acad. Sci. USA*, 86:4669–4673 (1989).

O'Sullivan et al., "Long–Term Anti–CD4 Treatment of MRL/lpr Mice Ameliorates Immunopathology and Lymphoproliferation but Fails to Suppress . . .", *Clin. Immunology and Immunopathology*, 61:421–435 (1991).

Prabhakar et al., "Cell Surface Expression of the 70–kD Component of Ku, a DNA–binding Nuclear Autoantigen", *J. Clin. Invest. Inc.*, 86:1301–1305 (1990).

Raz et al., "Cross–reactions of anti–DNA autoantibodies with Cell Surface Proteins", *Eur. J. Immunol.* 23:383–390 (1993).

Rekvig et al., "Intrinsic Cell Membrane Antigens Recognized by Antichromatin Autoantibodies", *Scan. J. Immunol.*, 29:7–13 (1989).

Ricotti et al., "Autoantibodies to purified nuclear proteins related to DNA metabolism during ageing and in SLE patients", *Immunology*, 61:375–381 (1987).

Sakharova et al., "Ontogenetic Changes in Spectrum of Specificities of Brain Reactive Monoclonal Natural Antibodies", *Zh. Obshch. Biol.*, 47:625–630 (1986) [English abstract only].

Walker et al., "Accelerated Appearance of Neoplasms in Female NZB/NZW Mice Treated with High–Dose Cyclophosphamide", *Arthritis and Rheumatism*, 22:1338–1343 (1979).

Walker et al., "Suppressed heterogeneous antinuclear antibody response in lymphoma–bearing NZB/NZW mice," *Clin. exp. Immunol.*, 24:210–217 (1976).

Banks et al. Characterization of cross reactive ∝–DNA autoantibodies in murine Lupus Immunol. Invest. 22:229, 1993.

Goding Mabs: Principles & Practice Production & Application of MAbs in Cell Biology, Biochem., +Immunol. Academic Press, 1986.

Winter et al. Abs against autologous tumor cell proteins in Patents with SCLC: Association with survival JNCI 85:2012, 1993.

Langdon et al. Characterization +Properties of a SCLC line Xenograft WX322 with Marked Sensitivity to ∝–IFN. Br. J. cancer 63:909, 1991.

Cronstein et al. The Adhesion Molecules of Inflammation Arthr. +Rheum. 36:147, 1993.

Osband et al. Problems in the Investigational Study + Clinical Use of Cancer Immunotherapy Immunol. Today 11:193, 1990.

Jain Barriers to Drug Delivery in Solid Tumors Sci Am 271:58, 1994.

Chatterjee et al. "Idiotypic Antibody Immunotherapy of Cancer", *Cancer Immunother.* 38:75–82, (1994).

Cronstein et al., "The Adhesion Molecules of Inflammation", *Arthritis and Rheumatism*, 36:147–157, (1993).

Goding, "Monoclonal Antibodies: Principles and Practice", Production and Application of Monoclonal Antibodies in Cell Biology, Biochemistry and Immunology, *Academic Press*, 2nd Edition, pp. 79–113, (1986).

Jain, Barriers to Drug Delivery in Solid Tumors, *Scientific American*, 271(1):58–65, (1994).

Langdon et al., Characterisation and properties of a small lung cancer cell line and xenograft WX322 with marked sensitivity to alpha–interferon, *Br. J. Cancer*, 63:909–915, (1991).

Osband et al., "Problems in the investigational study and clinical use of cancer immunotherapy", *Immunology Today*, 11:193–195, (1990).

Raz et al., "Cross–reactions of anti–DNA autoantibodies with Cell Surface Proteins", *Eur. J. Immunol. Today*, 11:193–195 (1990).

Winter et al., Antibodies Against Autoglous Tumor Cell Proteins in Patients With Small–Cell Lung Cancer: Association With Improved Survival, *J. Nat. Cancer Inst.*, 85:2012–2018, (1993).

Ricotti et al., "Autoantibodies to purified nuclear proteins related to DNA metabolism during ageing and in SLE patients", *Immunology*, 61:375–381 (1987).

*Primary Examiner*—Robert D. Budens
*Attorney, Agent, or Firm*—Fish & Richardson P.C.

[57] ABSTRACT

A method of inhibiting the growth of a tumor cell in a mammal by administering to the mammal an autoantibody, e.g. an antinuclear autoantibody from an aged mammal, that binds to either one or both of a surface of a tumor cell and a protein released from a dead tumor cell. Also disclosed are natural and monoclonal antinuclear autoantibodies from aged mammals and a hybridoma cell line producing a monoclonal antinuclear autoantibody.

23 Claims, 3 Drawing Sheets

USE OF AUTOANTIBODIES FOR TUMOR THERAPY AND PROPHYLAXIS

This is a continuation of application Ser. No. 08/265,411, filed Jun. 24, 1994, now abandoned.

BACKGROUND OF THE INVENTION

The invention relates to the use of autoantibodies for tumor therapy and prophylaxis.

Neoplasia is often caused by somatic mutations. When these mutations accumulate with age, the burden on the immune system, which controls neoplasia as one of its functions, is increased. However, despite increased cancer-related mortality rates in the aged, many aged individuals do not develop tumors. One explanation for this immunity is that certain natural antibodies play a role in humoral anti-tumor immunity (Chow et al., *Int. J. Cancer,* 27:459–469, 1981). However, little is known about the antigenic specificity of such antibodies.

One type of natural antibody found in the immune system is the autoantibody. These autoantibodies have been repeatedly found in significantly higher titers in older humans and laboratory animals without overt disease than in younger controls (Whitaker, et al., *Clin. Res.,* 14:143, 1966; Cammarata, et al., *JAMA,* 199:115–118, 1967; Siegel, et al., *Immunology,* 22:457–463, 1972). Hybridomas that produce natural autoantibodies from mice of different ages have been described (Sakharova, et al., *Zh. Obshch. Biol.,* 47:625–630, 1986).

The occurrence of autoantibodies in the aged is believed to serve as a marker of a disregulated immune system, and these antibodies recently have been prescribed with tumor growth-enhancing properties (Ben-Yehuda, et al., *Cancer Invest.,* 10:525–531, 1992). In earlier studies, others have noted that elevated levels of serum autoantibodies can result in the development of autoimmune systemic diseases (Dixon, et al., *Progress in Immunology,* 959–995, New York: Academic Press, 1980), and that antinuclear autoantibody suppression by the immunosuppressive drug cyclophosphamide may correlate with growth of a proliferating lymphoreticular neoplasm (Walker, et al., *Clin. Exp. Immunol.,* 24:210–217, 1976). Hahn et al., *Arthrit. Rheumat.,* 18:145–152 (1975), concluded that cyclophosphamide enhanced production of neoplasms such as lymphoreticular neoplasms, carcinomas, and sarcomas.

SUMMARY OF THE INVENTION

The invention is based on the discovery that natural antinuclear autoantibodies (ANA), e.g., from aged individuals, can be used to treat neoplasia, both existing tumors, and as a prophylactic measure. This protective effect was demonstrated for a natural monoclonal ANA (2C5) from an aged BALB/c mouse that dramatically inhibited the development of aggressive syngeneic EL4 T cell lymphoma in young mice, whereas control antibodies of the same isotype were without any effect.

The antibodies of the invention are characterized in that they (1) are autoantibodies, (2) bind to the surface of living tumor cells, e.g., EL4 T lymphoma cells, but not to normal T cells, (3) are antinuclear autoantibodies, i.e., bind to an antigen found in cell nuclei, e.g., a deoxyribonucleoprotein (DNP), and/or (4) bind to a protein, e.g., a DNP, released from dead tumor cells. The autoantibodies are found in higher titers in aged mammals, but can exist in young mammals as well.

In general, the invention features a method of inhibiting the growth, e.g., proliferation or actual increase in size, of a tumor cell in a mammal, e.g., a human, by administering to the mammal an autoantibody, e.g., an antinuclear autoantibody, that binds to either one or both of (1) a surface of a tumor cell, e.g., EL4, VERO neoplastic epithelial cells from green monkey kidney, a human lymphoma cell, a human myeloma cell, a human sarcoma cell, or the like, and (2) a protein released from a dead tumor cell, e.g, DNP. The autoantibody can be a substantially pure autoantibody isolated from serum from an aged mammal, such as a human or a murine mammal, or a monoclonal antibody produced by a hybridoma of a cell from an aged mammal.

The method can be used to treat various human tumor cells including a human sarcoma, myeloma, carcinoma, or lymphoma cell, and can include administration that occurs before a tumor cell is detected in the mammal, e.g., prophylactic administration to prevent the growth of tumor cells appearing in the mammal following administration of the autoantibody, or after a tumor cell is detected in the mammal, to prevent the further growth of tumor cells existing in the mammal prior to administration of the autoantibody.

The invention also features a method of determining whether an autoantibody is capable of inhibiting growth of a tumor cell, e.g., EL4, VERO neoplastic epithelial cell from green monkey kidney, a human lymphoma cell, a human myeloma cell, a human cell, a human sarcoma cell, or the like, by (a) obtaining a candidate autoantibody; (b) testing binding of the autoantibody to the surface of a tumor cell; and (c) testing binding of the autoantibody to a protein released from a dead tumor cell, e.g., a DNP, wherein the autoantibody is capable of inhibiting growth of a tumor cell when it tests positive in either one or both of steps (b) and (c).

The invention further features a method of inhibiting the growth of a tumor cell in a mammal, e.g., a human, by administering to the mammal an autoantibody linked, e.g., covalently or non-covalently bound, to a bioactive agent such as a cytotoxic agent or a cytokine. Cytotoxic agents include but are not limited to: saponin, ricin, ricin A-chain, abrin, abrin A-chain, diphtheria toxin, diphtheria toxin A-chain, exotoxin A-chain, daunomycin, daunorubicin, doxorubicin, mitomycin C, 5-fluorouracil, cytosine arabinoside, colchicine, cytochalasin B, bleomycin, vincristine, vinblastine, and methotrexate. Cytokines include, but are not limited to: interleukins, e.g., IL-2, growth factors, e.g., GM-CSF, and interferons, e.g., gamma interferon.

The invention also features a hybridoma cell which produces an autoantibody that inhibits tumor cell growth in a mammal. The autoantibody of the invention can be a polyclonal ANA from an aged mammal or a monoclonal antibody, e.g., antinuclear autoantibody 2C5, produced by a hybridoma cell, e.g., a hybridoma cell from the hybridoma cell line having the A.T.C.C. accession number CRL 11667. The autoantibody of the invention can be a substantially pure antibody.

By "substantially pure" is meant that the antibody provided by the invention is at least 60%, by weight, free from the proteins and naturally-occurring organic molecules with which it is naturally associated. Preferably, the preparation is at least 75%, more preferably at least 90%, and most preferably at least 99%, by weight, autoantibody. A substantially pure antibody may be obtained, for example, by extraction from a natural source such as mammalian, e.g., human, serum; preparation of a hybridoma cell producing the antibody, by expression of a recombinant nucleic acid encoding a monoclonal antibody, or by chemically synthesizing the protein. Purity can be measured by any appropriate standard method, e.g., column chromatography, polyacrylamide gel electrophoresis, or HPLC anlaysis.

As used herein, the phrase "autoantibody from an aged mammal" means a natural autoantibody taken directly from a mammal that is old, i.e., one that has lived 60% or more of the life span expected for that species. This phrase also encompasses autoantibodies produced by a cell taken from an old mammal or progeny of that cell, for example, by generation of hybridoma cells.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

Other features and advantages of the invention will be apparent from the detailed description, and from the claims.

DETAILED DESCRIPTION

Figure 1A:
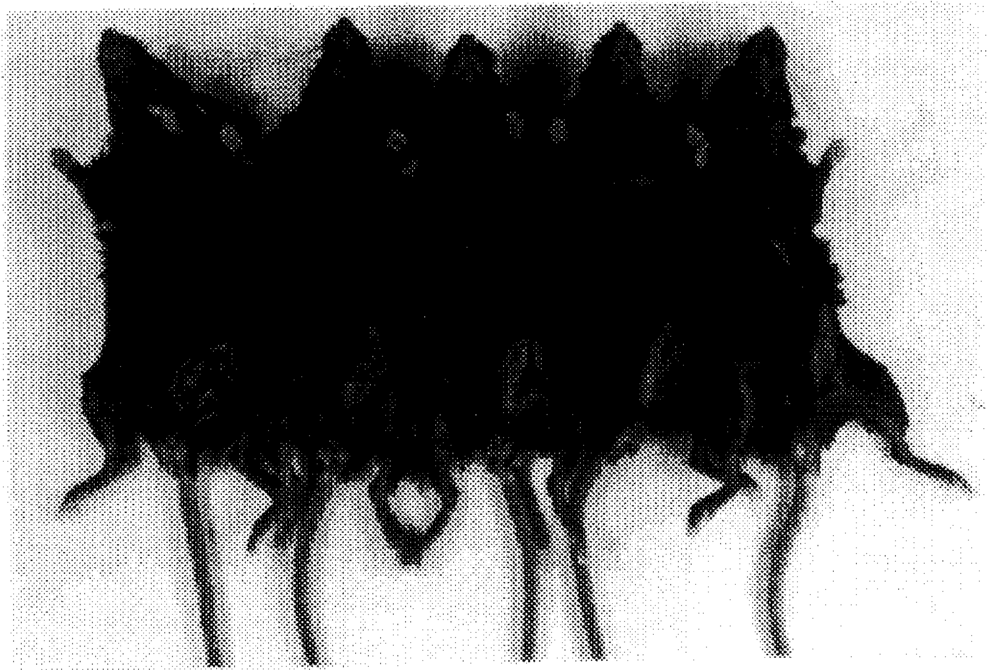
FIGS. 1A and 1B are photographs of five mice showing suppression of tumor growth in the presence of monoclonal ANA 2C5 and extensive tumor growth in the presence of an isotype matched control antibody, respectively.

Applicants have discovered that natural autoantibodies, such as ANA from aged individuals, can be used to treat existing tumors and as a prophylactic measure to prevent tumors or their metastases. There now follows a description of the isolation and characterization of ANA from an aged mouse, and the production and testing of monoclonal ANA from mice for use in the inhibition of tumor cell growth in a mammal. These examples are provided for the purpose of illustrating the invention, and should not be construed as limiting. Moreover, the techniques can be applied generally to the isolation, characterization, and use of autoantibodies from human serum, and the production of human monoclonal autoantibodies.

Autoantibodies

The autoantibodies, e.g., ANA, can be from any mammalian species, including, murine, human or the like, or combinations thereof, such as chimeric antibodies, having a human constant region and a mouse or other mammalian source variable region. The important characteristic is that the autoantibody binds specifically to the surface of living tumor cells, e.g., EL4 T lymphoma cells, but not to normal T cells, or binds to a protein, e.g., deoxyribonucleoprotein, released from the dead tumor cells.

Detection of ANA by Indirect Immunofluorescent Test

ANA can be detected in the sera of mammals, e.g., human patients, using an indirect immunofluorescence procedure that involves the use of mammalian liver substrate, e.g., rat liver or human liver cell line HEP2. In this procedure, human serum is placed on a cryostat section of rat liver that permits attachment of immunoglobulin molecules with antinuclear specificity. The slide with the rat liver sections is washed with phosphatebuffered saline (PBS) and the fluorescein-conjugated goat anti-human IgG (Antibodies Inc.) is added. After washing again with PBS, the fluorescein-conjugated goat anti-human IgG is visualized by fluorescence microscopy. Serum samples are diluted with PBS; the highest titer that produces a positive test for ANA is used as the ANA titer.

The pattern of immunofluorescence often corresponds to a particular antigen against which the antibodies are directed. For example, a homogeneous pattern of immunofluorescence in the cell nucleus suggests the presence of antibodies directed against DNA or certain DNA binding proteins such as histones. A speckled pattern is characteristic of antibodies directed against nuclear ribonucleoproteins (nRNP) such as Sm, Ro, and La antigens.

Preparation of Antibodies

Once detected and isolated, autoantibodies, e.g., ANA, can be obtained as monoclonal autoantibodies by hybridoma formation and expression in the hybridoma supernatant culture, or produced by ascites. The antibody can also be a monoclonal antibody fragment, such as FAB, $F(ab_2)$, Fv, a recombinant variable region, or the like.

ANA from an aged mammal are prepared by pooling sera of an immune mammal or mammals, e.g., a mouse or a human, followed by fractionation of the IgG component from the plasma or sera. Human or mouse monoclonal antibody producing cell lines can be prepared by standard transformation and hybridoma technology (see, e.g., *Methods in Enzymology, Vol.* 121, Sections I and II (1986) eds. J. J. Langone and H. V. Vunakis, Academic Press).

Monoclonal natural ANA 2C5 (2C5) from non-immunized healthy, aged mice was obtained and characterized as belonging to the subclass IgG2a (Sakharova, et al., *Zh. Obshch. Biol.,* 47:625–630, 1986). 2C5 was obtained as follows. Splenocytes from two non-immunized healthy aged (26 months old out of an average life span of up to 30 months) female Balb/c mice were fused with murine myeloma cell line P3X63-Ag8.653 (ATCC No. CRL1580). Several hundred resulting hybridoma clones were tested for autoreactivity in a standard radioimmunoassay with homogenates of different tissues (liver, kidney, brain). Homogenates of these organs were incubated with the supernatants of the hybridoma clones, washed three times in phosphate-buffered saline with 3% bovine sera albumin (PBS-3), incubated with 125-I-labeled anti-mouse antibodies in PBS-3, washed three times in PBS-3 and analyzed in a γ-counter. About 5% of hybridomas obtained were positive in this test, and were positive with all three targets. Thus, these antibodies are not tissue-specific, and are clearly autoantibodies.

Further characterization of the target of 2C5 was achieved in a test of indirect immunostaining of mouse or rat brain slices. Cryostat slices were fixed in acetone, washed 3×5 minutes in PBS-3, incubated for 20 minutes with hybridoma supernatants, washed, and incubated with horseradish peroxidase-labelled anti-mouse antibodies. Color reaction was developed with 3,4 diaminobenzidine in a standard procedure.

All the hybridomas found to be positive in the radioimmunoassay with homogenates were also positive in an immunocytochemistry study of mouse or rat brain slices, showing reactivity with the nuclei of all the cells. In contrast, no antinuclear reactivity was seen with homogenates-positive hybridomas obtained in a similar procedure from newborn (4–5 days old) or adult (6 months old) non-immunized healthy mice. Homogeneous, but not speckled, patterns of nuclear staining indicated that the antibody's target is DNA or some DNA-bound protein. Thus, the autoantibody was also an antinuclear autoantibody (ANA).

Hybridoma 2C5 was chosen for further analysis because it showed intensive nuclear reactivity and high reactivity with the surface of transformed tumor cell lines from in vitro or ex vivo cultures such as EL4 mouse thymoma, S49 mouse T lymphoma, P3X63-Ag8.653 mouse myeloma, and a VERO neoplastic epithelial cell line from green monkey kidney. The hybridoma producing this monoclonal antibody was deposited on Jun. 22, 1994 with the A.T.C.C. in Rockville, Md., under the Accession No. CRL 11667.

Monoclonal antibody 2C5 and the isotype matched control antibody, UPC10, (Cappel, Durham, N.C.) were purified from ascites fluid by precipitation with 40% ammonium sulfate, or further purified using ion-exchange chromatography on CM-agarose (Pharmacia Biotech, Inc., Piscataway, N.J.) using standard techniques well known to those skilled in the art (see, e.g., Jiskoot et al., "Two-Step Purification of a Murine Monoclonal Antibody Intended for Therapeutic Application in Man", *J. Immunol. Methods,* 124:143–156, 1989; Ausubel et al., *Current Protocols in Molecular Biology*, John Wiley & Sons, N.Y., 1989; and Fisher, *Laboratory Techniques in Biochemistry and Molecular Biology*, eds., Work and Burdon, Elsevier, 1980).

The antibody purity was characterized with HPLC using standard techniques. Both ammonium sulfat-eprecipitated and ammonium sulfate/CM-agarose-purified preparations gave similar results in in vivo experiments.

Humanizing Antibodies

Since, for the most part, monoclonal antibodies are produced in species other than humans, they are often immunogenic to humans. In order to successfully use these monoclonal antibodies in the treatment of humans, it may be necessary to create a chimeric antibody molecule wherein the portion of the polypeptide involved with ligand binding (the variable region) is derived from one species, and the portion involved with providing structural stability and other biological functions (the constant region) is derived from a human antibody. Methods for producing chimeric antibodies in which the variable domain is derived from one host and the constant domain is derived from a second host are well known to those skilled in the art. See, for example, Neuberger et al., WO Publication No. 86/01533, priority 9/3/84; Morrison et al., EP Publication No. 0 173 494, priority 8/27/84.

An alternative method, in which an antibody is produced by replacing only the complementarily determining regions (CDRs) of the variable region with the CDRs from an immunoglobulin of the desired antigenic specificity, is described by Winter (GB Publication No. 2 188 638, priority 3/27/86). Murine monoclonals can be made compatible with human therapeutic use by producing an antibody containing a human Fc portion (Morrison, S. L. (1985) *Science* 229:1202–1207). Established procedures allow construction, expression, and purification of such a hybrid monoclonal antibody. Regimens for administering immune globulin therapeutically have previously been used for a number of infectious diseases.

In addition, antibodies can be generated by non-human mammalian hosts that contain xenogeneic human DNA segments encoding human Ig loci for response to immunogens according to the protocol in Kuncherlapati et al., WO 94/02602.

As used herein, the term "antibody" is meant to encompass monoclonal or polyclonal antibodies, whole, intact antibodies or antibody fragments having the immunological activity of the whole antibody. Also encompassed within the term "antibody" are chimeric antibodies having the variable and constant from different host species, or those wherein only the CDRs are replaced.

Human Monoclonal Antibodies

Some human ANA give a homogeneous pattern of nuclear staining and react with cell plasma membranes, similar to 2C5 (Rekvig, *Scand. J. Immunol.,* 29:7–13, 1989). Thus, hybridomas of completely human origin that produce human autoantibodies, e.g., ANA, can be obtained by fusing B cells (e.g., peripheral blood B cells) from an ANA-positive healthy, aged individual with a human "fusion partner" cell line such as UC 729-6 or SHFP-1 as described in McKnight et al., *Human Antibodies and Hybridomas,* 1:77–82 (1990).

Testing Anti-Tumor Autoantibodies

Anti-tumor autoantibodies that fall within the scope of the present invention can be characterized using the following standard assays. First, they must be autoantibodies, which can be determined using standard tests for autoantibodies, e.g., ELISA with standard autoantigens. Second, they must bind to the surface of a tumor cell and/or a protein released by dead tumor cells. These two binding characteristics can be determined using standard flow cytometry techniques and an ELISA assay, respectively, as described below.

Assay for Tumor Cell Surface Binding

The binding of a monoclonal ANA (e.g., 2C5 described above, or a monoclonal ANA from an aged mammal such as a human) to tumor cells (e.g., lymphoma or other tumor cell, where the tumor cell is from a mouse or a human) was monitored by flow cytometry using standard techniques. This assay can be used to determine whether a given ANA binds to a tumor cell surface antigen, and to determine whether a given tumor cell can be treated with a selected ANA.

Cell viability at the start of the procedure was more than 95% as determined by a standard Trypan Blue exclusion test.

Cells in single cell suspensions (EL4 T lymphoma, S49 T lymphoma, and P3X63-Ag8.653 myeloma) or in monolayers (for non-suspension cells such as VERO cells (green monkey kidney epithelium tumor) were incubated for 20 minutes with monoclonal antibody 2C5 or isotype matched control myeloma antibody UPC10 (5–10 μg/ml in culture media with 10% bovine calf serum (CM10, HyClone, Logan, Utah), washed twice in HBSS (Cellgrow, Herndon, Va.), incubated 20 minutes with FITC-labelled F(ab)2 fragments of goat anti-mouse antibodies (Cappel) (diluted 1:100 with CM10), again washed twice with HBSS, and fixed in a 4% paraformaldehyde solution in PBS and studied using a fluorescent microscope or flow cytometer. All the procedures were carried out at 20° C.

Cells were analyzed using a FACSCAN analyzer (Becton Dickinson and Co., Bedford, Mass.), and were life gated using forward and side scatter to exclude debris and dead cells according to manufacturers instructions. Life gating is a standard hardware or software program that allows analysis of only living cells. The reaction with the surface of attached VERO cells was examined only with a fluorescent microscope. A trypan blue exclusion test was used to exclude the reactivity due to any interaction with intracellular antigens. The reaction of 2C5 with cell surface antigens of suspension cells EL4 thymoma, S49 T lymphoma, and P3/Ag8.653 myeloma, was demonstrated both with the microscope and with the flow cytometer.

Figure 2A:
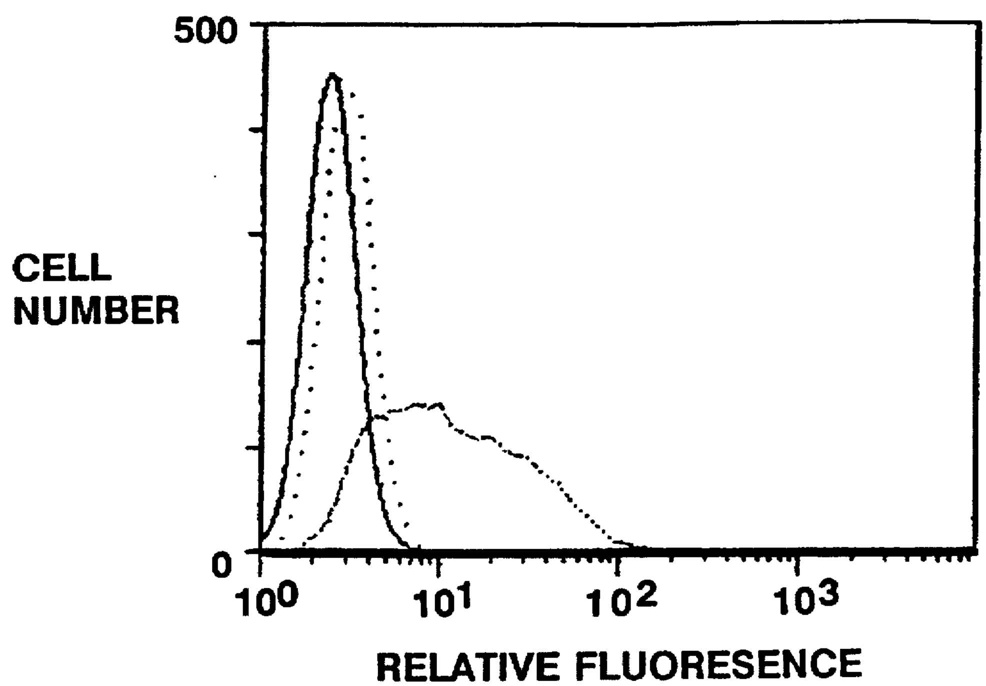
FIGS. 2A and 2B are graphs showing flow cytometric analysis of monoclonal ANA 2C5 binding to EL4 T cell lymphoma cells from an in vitro culture, and lack of binding to thymocytes from 5 week old mice, respectively.
Figure 2B:
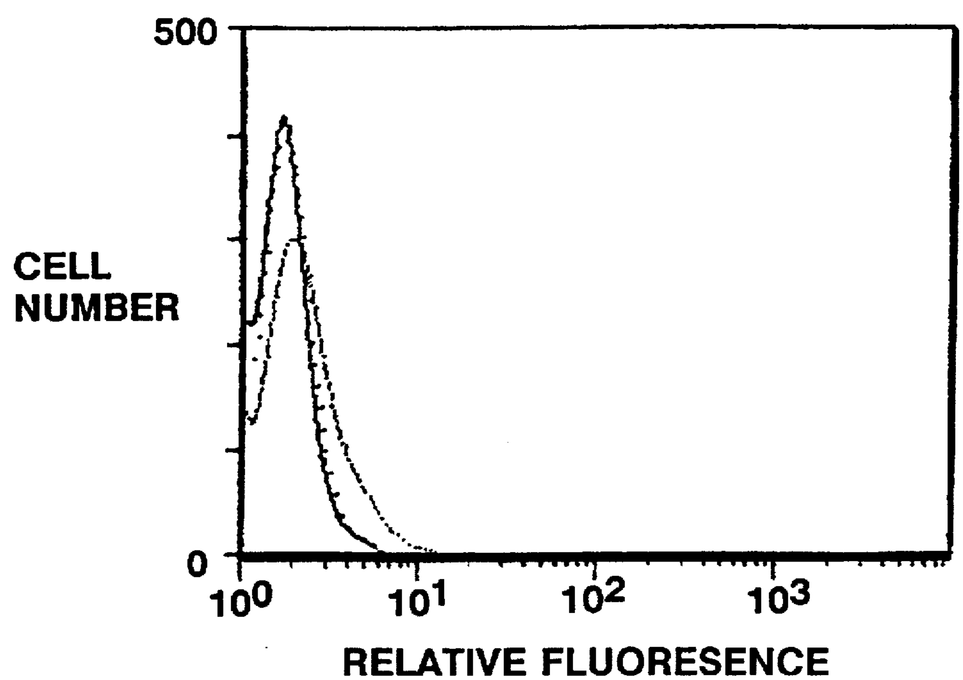

As shown in FIG. 2A, monoclonal antibody 2C5 bound to EL4 T cell lymphoma from an in vitro culture, but did not bind to thymocytes from an intact 5 weeks old C57BL/6 mouse (FIG. 2B). In these two graphs, the relative fluorescence of FITC-labeled anti-mouse F(ab)2 fragments alone is shown as a solid line, of control antibody UPC10 plus FITC-labeled anti-mouse F(ab)2 fragments is shown as a widely dotted line, and of the 2C5 plus FITC-labeled anti-mouse F(ab)2 fragments is shown as a closely dotted line. Thus, FIG. 2A shows increased relative fluorescence only for the closely dotted line, and FIG. 2B shows no increased relative fluorescence.

Figure 3:
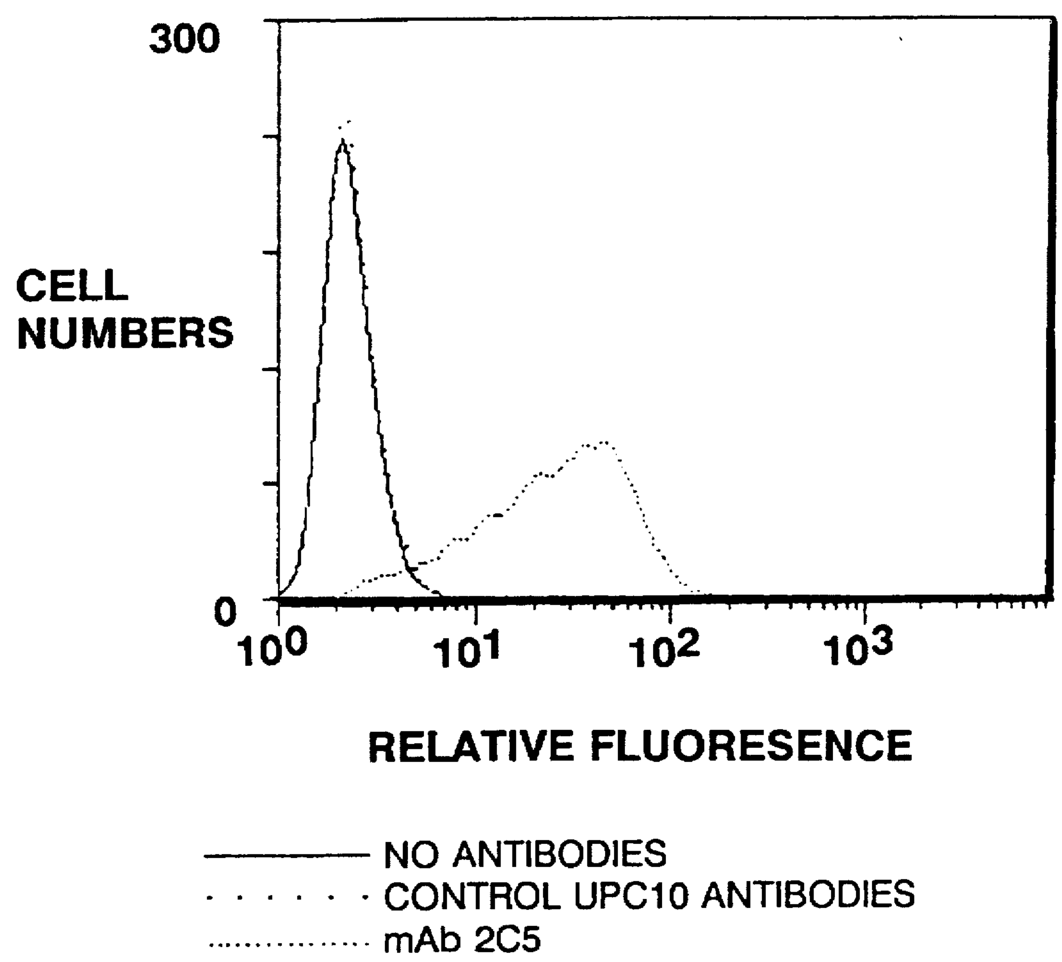
FIG. 3 is a graph showing flow cytometric analysis of monoclonal ANA 2C5 binding to S49 T cell lymphoma cells from an in vitro culture.

As shown in FIG. 3, 2C5 also bound to S49 T lymphoma (closely dotted line) whereas control antibody UPC10 did not. Antibody 2C5 also bound to P3/Ag8.653 myeloma and green monkey kidney epithelium tumor cells. Based on these results, 2C5 should also bind to other tumor cells, including human tumor cells.

ELISA Assay

A standard ELISA assay can be used to determine whether a given autoantibody binds to nuclear antigens and/or proteins released from dead cancer cells. Nuclear antigens for anti-tumor ANA such as 2C5 include histones, which play a structural role in chromatin organization, and non-histone proteins regulating DNA transcription and replication such as La- and Ku-antigens.

The interaction of monoclonal antibody 2C5 with various nuclear autoantigens was tested with 96-well plates coated with the nuclear autoantigens listed in Table 1 below obtained from Diamedix Corp., Miami, Fla. The coating of ELISA plates with autoantigens released from the dead EL4 lymphoma cells was performed by 1 hour incubation with the supernatant from dead cells. To prepare the supernatant, $2\times10^6$ EL4 cells were cultivated for 16 hours at 37° C. and 7% $CO_2$ in 1 ml of HBSS. Antigen-coated wells were washed and incubated for 30 minutes with PBS-T solution (phosphate-buffered saline with 0.05% v/v of TWEEN® 20). The tested antibody (0.5 mg in 100 ml of PBS-T) was added to each well. The bound material was detected by adding peroxidase-labeled goat anti-mouse antibody (Cappel, Durham, N.C.) followed by the substrate. Absorbance in the visible spectrum at 405 nm was recorded using a Multiscan reader (Flow Labs., East Costa Mesa, Calif.) as an indication of relative reactivity in each well. Only the reactions giving an absorbance value at 405 nm, and which were five standard deviations above background absorbance, were scored as positive and marked with "+"(Table 1).

TABLE 1

Reactions of 2C5 With Intracellular Autoantigens in ELISA

| | Antigen | | | | | | | |
|---|---|---|---|---|---|---|---|---|
| Antibody | Dead EL4 cells | DNP | DNA | La | Ro | Sm | Jo-1 | Scl-70 |
| 2C5 | + | + | – | – | – | – | – | – |
| UPC10 | – | – | – | – | – | – | – | – |

As shown in Table 1, 2C5 bound only to the supernatant from dead EL4 cells and to DNP (Diamedix Corp.). Control antibody UPC10 did not bind to any of the antigens.

Anti-Tumor Effect of Autoantibodies

Tumors

A population of mammalian (preferably human or mouse) cancer cells (e.g., lymphoma, carcinoma, sarcoma, or myeloma) can be used to test the anti-tumor effect of an autoantibody such as an ANA from an aged mammal. The EL4 T cell lymphoma was selected for testing in C57BL mice because it is extremely aggressive, i.e., only about 10 tumor cells are sufficient to kill a mouse, and it is resistant to known methods of chemotherapy (Tarnovski, et al., *Cancer Res.*, 39:3964–3967, 1979). In addition, mice do not have natural antibodies reactive against EL4 cells (Pierotti, et al., *Int. J. Cancer*, 18:223–229, 1976), and mice do not develop conventional antibodies against this virtually non-immunogenic tumor (Rees, et al., *Chemotherapy*, 28:283–290, 1982). Thus, this type of tumor is one of the most difficult to treat, and was selected for testing for this reason.

Tumor Inhibition In Vitro

The effect of a given autoantibody or ANA on the growth of a selected tumor cell, e.g., from a human patient, is tested in vitro using standard techniques well known in the art. For example, cells of a human cancerous tumor are extracted from the patient and cultured in vitro by standard techniques in the appropriate culture medium. The autoantibody, e.g., an ANA from an aged mammal (where the ANA is natural or monoclonal and the mammal is a mouse or human, for example) is contacted in vitro with the cultured human tumor cells in the presence of immune system effectors, e.g., murine or human, such as complement and/or cytotoxic cells, e.g., neutrophils and macrophages.

Growth is determined, e.g., by monitoring the incorporation of derivatives of labelled exogenous thymidine, e.g., (methyl[$^3$H] thymidine 15 Ci $mmol^{-1}$) (Amersham International, U.K.) into the DNA of treated and control tumor cell cultures. See, e.g., Curtin et al., *Br. J. Cancer*, 53:361–368 (1986). Standard cytotoxicity testing can be used to determine the percentage of dead cells in the culture. For example, the selective release of labelled chromium (e.g., $Na_2{}^{51}CrO_4$, Amersham, Arlington Heights, Ill.) from dead cells into the culture medium can be monitored.

Tumor Inhibition In Vivo

In vivo testing of the effect of a selected autoantibody on the growth of human or other tumor cells is performed in humans or, preferably in an immunosuppressed animal, e.g., a nude mouse, carrying a xenogeneic tumor which has proliferated from artificially implanted tumor cells, e.g., tumor cells from a human, a mouse, or other mammal. The autoantibody, e.g., an ANA from an aged mammal, is formulated in a physiologically acceptable carrier, and injected into the mouse carrying the tumor and proliferation is monitored.

For example, the following nude mouse assay can be used to test the anti-tumor effect of a selected ANA on a particular human tumor. Male athymic nude BALB/c mice (21–24 g)(Life Sciences, St. Petersburg, Fla.) are housed in a pathogen-free, temperature-controlled isolation compound and exposed to a light-controlled day (lights on, 0700–1900 h). Diet can be composed of standard chow (Autoclavable Rodent Chow No. 5010; Ralston Purina, St. Louis, Mo.) and water given ad libitum.

The tumor is xenografted as 2-$mm^2$ pieces s.c. through an interscapular incision bilaterally into the flanks (two tumors per mouse) of 12 anesthetized mice. Mice are weighed weekly, and tumors are measured twice weekly with calipers, and tumor surface areas calculated using the product of the two greatest perpendicular tumor diameters. Tumor doubling times are calculated from semilogarithmic graphs of tumor area versus days from implantation. At termination of the experiment, mice are sacrificed by cervical dislocation followed by excision of tumors and pancreas. Tissues are frozen in liquid nitrogen and stored at −70° C. until assayed.

Mice with implanted tumors are randomized and divided into two groups, each receiving 0.1 ml i.p. injections 3 times per week. The control mice receive saline and the mice in the treatment group receive the selected ANA in saline (e.g., 50 to 1000 μg, preferably 400 to 500 μAg, per injection, per mouse).

The following test was carried out to demonstrate the anti-tumor effect of 2C5 on EL4 T cell lymphoma in mice. To simulate the natural situation of the aged mice, in which the neoplastic cells appear in a background of elevated serum ANA, experimental young mice were injected with 2C5 one day before (day −1) tumor cell inoculation. Additional injections on days 1, 3, and 5 were used to maintain a sufficient level of the monoclonal antibody during early events of tumor development.

Experimental and control mice received a single inoculation of cultured EL4 lymphoma cells on day 0 ($0.02\times10^6$ cells in 0.5 ml Hanks buffered salt solution (HBSS) per mouse). Antibodies formulated in a physiologically acceptable carrier were injected intraperitoneally on days −1, 1, 3, and 5 (70 mg of purified antibody in 0.5 ml HBSS per mouse per injection). Mice were sacrificed by cervical dislocation on day 15 after the injection of $0.02\times10^6$ tumor cells, and on day 13 after the injection of $0.2\times10^6$ and $2\times10^6$ tumor cells. During the experiment animals were kept on a standard diet. Tumor size and appearance was recorded by photography, following which, subcutaneous tumors were cut out and weighed. Statistical analysis of relative tumor weight was performed to calculate "p" values (see, e.g., Siegel, *Nonparametric Statistics for the Behavioral Sciences*, pp. 152–158. New York: McGraw-Hill Book Company, Inc., 1956).

Figure 1B:
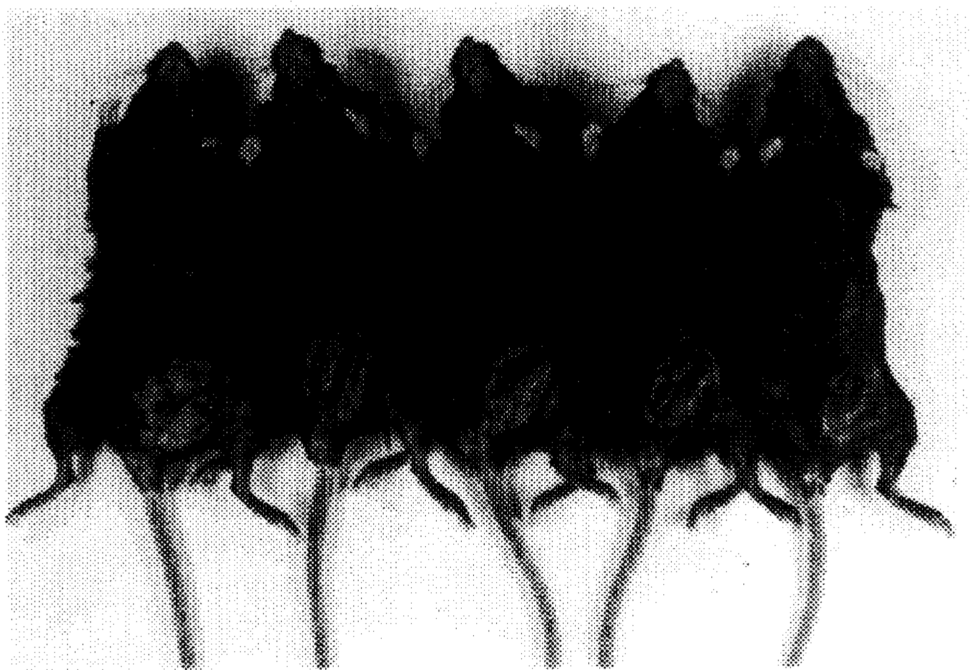

Monoclonal antibody 2C5 purified from both ascites or sera-free hybridoma supernatant was effective in the suppression of the development of the syngeneic EL4 lymphoma in C57BL/6 mice compared to control mice injected with isotype matched antibody produced by UPC10 myeloma (Cappel). The rate of subcutaneous tumor growth was substantially inhibited. Less than 25 per cent of experimental mice injected with 20,000 EL4 lymphoma cells developed subcutaneously growing tumors after 15 days, compared with at least 75 per cent in controls (FIGS. 1A and 1B and Table 2).

TABLE 2

In Vivo Suppression of Tumor Growth by Monoclonal 2C5

| Number of EL4 cells injected | Treatment with | Number of mice with tumor | Tumor weight, g |
|---|---|---|---|
| $0.02 \times 10^6$ | HBSS | 13/17* | $1.58 \pm 0.64$ |
| | UPC10 | 5/5 | $1.56 \pm 0.17$ |
| | 2C5 | 4/18** | $0.16 \pm 0.07$ $p < 0.005$ |
| $0.2 \times 10^6$ | HBSS | 3/4 | $1.30 \pm 0.58$ |
| | UPC10 | not done (ND) | ND |
| | 2C5 | 2/5 | $0.42 \pm 0.29$ $p < 0.1$ |
| $2 \times 10^6$ | HBSS | 4/4 | $1.38 \times 0.23$ |
| | UPC10 | ND | ND |
| | 2C5 | 3/4 | $0.94 \pm 0.30$ $p < 0.15$ |

*Cumulative data from three experiments, 5–6 mice in each.
**Cumulative data from four experiments, 4–6 mice in each.

The inhibition of tumor growth gradually decreased with the increase in the amount of lymphoma cells injected, from $0.02\times10^6$ to $2\times10^6$ cells per mouse (Table 2). These data evidence the prophylactic role of ANA from an aged animal in the control of natural tumor growth or development of metastases.

To further demonstrate the prophylactic effect of a selected autoantibody, it can be administered in a pharmaceutically acceptable carrier to normal animals at regular intervals to maintain a relatively constant level of the antibody in the blood. The animals are then exposed to a known carcinogen or specific amount of UV radiation that induces the development of cancer cells in control animals at a known rate. Similarly, known transgenic animals that are bred to develop tumors can be used to test the prophylactic effect of an autoantibody.

The binding characteristics of 2C5 described above provide evidence for two different potential mechanisms underlying the anti-tumor activity. First, flow cytometry data (FIGS. 2A and 2B) demonstrated that 2C5 binds with the surface of living EL4 T lymphoma cells, but not normal T cells. In addition, 2C5 binds to the surface of a variety of other tumor cells such as S49 T lymphoma, P3X63-Ag8.653 myeloma, and VERO cells (green monkey kidney epithelium tumor cell line), which indicates that the antigenic determinant recognized by monoclonal antibody 2C5 is evolutionarily conserved (Klinman, *J. Immunol.*, 148:1353–1358, 1992).

Different possible mechanisms for interaction of autoantibodies such as ANA with the cell surface have been described. Among these are the expression of a nuclear antigen on the cell surface (Prabhakar, et al., *J. Clin. Invest.*, 86:1301–1305, 1990; Bachman, et al., *Exp. Cell Res.*, 191:171–180, 1990), the possible cross-reactivity between nuclear and cell surface antigens (Lafer, et al., *J. Exp. Med.*, 153:897–909, 1981), and binding of ANA to the cell surface as a part of an immunocomplex (Jacob, et al., *Proc. Natl. Acad. Sci. USA*, 86:4669–4673, 1989). Whatever the mechanism of interaction, the data obtained support a conclusion that 2C5, which belongs to the immuno-aggressive IgG2a isotype (Scholz, et al., *Cancer Immunol. Immunother.*, 33:153–157, 1991), mediates antibody-dependent cellular cytotoxicity or/and complement-dependent lysis of tumor cells in vivo. Other isotypes such as IgG3 should also work. The class of IgG to which a given autoantibody belongs can be determined using standard techniques.

Second, 2C5 reacts with a protein released into the culture medium from dead tumor cells in vitro (Table 1). This finding supports another possible mechanism for the in vivo action of 2C5 on tumor development that can act concurrently with the complement-dependent lysis. It is known that, together with a large number of proliferating cells, every tumor contains some dead or dying cells (Wyllie, A. H., *Anticancer Res.*, 5:131–136, 1985). Intracellular antigens released from the dead cells enter the circulation and create high local concentrations in the tumor blood vessels. Autoantibodies in the blood form immune complexes with some of those intracellular antigens, thereby elevating the local concentration of such complexes in the tumor vasculature. These complexes provide a local stimulation of the effector immune cells such as natural killer cells, neutrophils, and macrophages, which strongly inhibit further tumor development.

Use

Existing tumors are treated in vivo by the administration (preferably by either intravenous or subcutaneous injection) of an anti-tumor autoantibody, e.g., an ANA of murine or human origin, formulated in a physiologically acceptable carrier. The proper dosage for therapeutic administration is determined by a physician for each case depending on the particular patient's age and weight, and on the size of the tumor. The dosage is within a range of 1 to 20 mg/kg of body weight of the patient to ensure that binding sites in the blood and on the surface of the tumor cells are saturated. Administration is continued until the tumor is destroyed, or used as an adjunct to other anti-tumor therapy or surgery until the tumor is destroyed or removed.

Once a malignant tumor is located, the autoantibodies can also be used advantageously to prevent a secondary metastatic growth of the tumor. In this application, the antibodies are administered at periodic intervals to provide a relatively constant level of the antibodies in the blood stream until the original tumor is destroyed by the effect of the autoantibodies, or is removed surgically or by chemotherapy. The half-life of the autoantibodies in a mammal, e.g., a human, is on the average of several days, so a new dosage of autoantibodies should be administered about once every 3 to 7 days, depending on the particular antibody. The specific regimen is based on standard blood tests that indicate the level of the autoantibody in the bloodstream. The dosage per injection is in the range of 1 to 20 mg/kg of body weight of the patient.

For other prophylactic uses, e.g., prior to the existence of a proliferating tumor, the dosage is again determined by a physician, but would be somewhat lower than the dosage required when a tumor is present, e.g., within a range of 0.1 to 5.0 mg/kg of body weight of the patient, depending on the patient's potential susceptibility to tumors based on, e.g., family history and DNA testing.

Human anti-tumor autoantibodies isolated from serum of healthy aged humans and administered directly, or in the form of human monoclonal antibodies derived from aged human cells, should have little, if any, toxic effects.

Deposit Statement

The hybridoma culture that produces monoclonal antibody 2C5 was deposited on Jun. 22, 1994 with the A.T.C.C. in Rockville, Md. under accession number ATCC CRL 11667. This culture is maintained under conditions that assure that access to the culture will be available during the pendency of this patent application to one determined by the Commissioner of Patents and Trademarks to be entitled thereto under 37 CFR 1.14 and 35 USC 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep the cells viable and uncontaminated for a period of at least five years after the most recent request for the furnishing of a sample of the deposits, and in any case, for a period of at least 30 (thirty) years after the date of deposit or for the enforceable life of any patent which may issue disclosing the culture plus five years after the last request for a sample from the deposit. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing them.

Other Embodiments

It is to be understood that while the invention is described in conjunction with the detailed description thereof, that the foregoing description is intended to illustrate and not limit the scope of the invention, which is defined by the scope of the appended claims. Other aspects, advantages, and modifications within the scope of the invention will be apparent to those skilled in the art to which the invention pertains.

For example, the anti-tumor autoantibodies of the invention can also be used as tumor cell targeting agents that can be attached to known anti-tumor bioactive agents to augment the natural anti-tumor effect demonstrated for these autoantibodies themselves.

For example, the autoantibodies can be covalently linked to cytotoxins such as saponin, ricin, ricin A-chain, abrin, abrin A-chain, diphtheria toxin, diphtheria toxin A-chain, exotoxin A-chain, daunomycin, daunorubicin, doxorubicin, mitomycin C, 5-fluorouracil, cytosine arabinoside, colchicine, cytochalasin B, bleomycin, vincristine, vinblastine, methotrexate, and other natural and synthetic, commercially available cytotoxins (Sigma Chemical Co., St. Louis, Mo., for example) known to those of ordinary skill in the art.

The autoantibodies also can be linked to cytokines such as interleukins, e.g., IL-2, interferons, e.g., gamma interferon, and growth factors, e.g., GM-CSF (Genzyme, Cambridge, Mass.).

The bioactive agent can be linked by a cleavable bond to the antibody if the toxin is internalized by the cancer cell to have an effect. For example the cleavable bond is enzymatically labile (such as a peptide linkage) for antibody-cytotoxin or antibody-cytokine complexes that are internalized into the cell's cytoplasm or susceptible to hydrolysis by enzymes of the extracellular matrix. The bond may be pH labile for complexes that are phagocytized into the low pH environment of a lysosome.

The antibody is linked directly or indirectly to the bioactive agent by a carrier molecule such as serum albumin (particularly human serum albumin), polyamino acids and dextran by methods well known to those of ordinary skill in the art. Convenient linkages include disulfides, imides, hydrazones, amides, and the like. Multiple bioactive agent can be linked to the antibody. The multiple agents may be the same molecule or a mixture of agents linked to the antibody. The number of molecules linked to the antibody can vary depending on the size of the bioactive agent.

The autoantibody-cytotoxin or autoantibody-cytokine complex is administered to the mammal for the purpose of inhibiting tumor cell proliferation as described above for the antibody alone.

What is claimed is:

1. A method of inhibiting the growth of a tumor cell in a mammal, said method comprising administering to the mammal an antinuclear autoantibody obtained from a non-immunized, healthy mammal or from a hybridoma prepared with cells from a non-immunized, healthy mammal, wherein said autoantibody binds specifically to (i) a surface of a living tumor cell and (ii) a protein released from a dead tumor cell or an antigen in the nucleus of said tumor cell, and (iii) does not specifically bind to the surface of normal cells of the mammal to which it is administered.

2. A method of claim 1, wherein said autoantibody is a substantially pure autoantibody isolated from serum from an aged mammal.

3. A method of claim 2, wherein said aged mammal is a human.

4. A method of claim 2, wherein said aged mammal is a murine mammal.

5. A method of claim 1, wherein said dead tumor cell protein is a deoxyribonucleoprotein.

6. A method of claim 1, wherein the mammal is a human.

7. A method of claim 6, wherein said tumor cell is a human sarcoma, myeloma, carcinoma, or lymphoma cell.

8. A method of claim 1, wherein said administration occurs before a tumor cell is detected in the mammal.

9. A method of claim 1, wherein said administration occurs after a tumor cell is detected in the mammal.

10. A method of claim 1, wherein said autoantibody is a monoclonal antibody produced by a hybridoma of a cell from an aged mammal.

11. A method of claim 10, wherein said aged mammal is a murine mammal.

12. A method of claim 10, wherein said aged mammal is a human.

13. Hybridoma cell line having A.T.C.C. accession number CRL 11667.

14. Monoclonal antibody 2C5 produced by the hybridoma cell line of claim 13.

15. A method of determining whether a candidate antinuclear autoantibody is capable of inhibiting growth of a tumor cell, said method comprising the steps of:

(a) determining whether said candidate antinuclear autoantibody specifically binds to the surface of a living tumor cell;

(b) determining whether said candidate antinuclear autoantibody specifically binds to the surface of a normal cell;

(c) determining whether said candidate antinuclear autoantibody specifically binds to a protein released from a dead tumor cell or an antigen in the nucleus of said tumor cell, wherein said candidate antinuclear autoantibody is capable of inhibiting growth of a tumor cell when specific binding occurs in both of steps (a) and (c), but does not occur in step (b).

16. A method of claim 15, wherein said dead tumor cell protein is a deoxyribonucleoprotein.

17. A method of claim 1, wherein said autoantibody is linked to a bioactive agent.

18. A method of claim 17, wherein said bioactive agent is a cytotoxic agent.

19. A method of claim 17, wherein said bioactive agent is a cytokine.

20. A method of obtaining an antinuclear autoantibody that inhibits growth of a tumor cell, said method comprising (a) obtaining an antinuclear autoantibody from a non-immunized, healthy mammal by preparing an affinity column comprising a nuclear antigen as a ligand;

(b) passing sera through said column to bind antinuclear autoantibodies to said nuclear antigen;

(c) releasing said bound antinuclear antibodies from said column; and thereafter (d) determining whether said autoantibody specifically binds to the surface of a living tumor cell;

(e) determining whether said autoantibody specifically binds to the surface of normal cells; and (f) determining whether said autoantibody specifically binds to a protein released from a dead tumor cell or an antigen in the nucleus of said tumor cell, wherein said autoantibody is capable of inhibiting growth of a tumor cell when specific binding occurs in both of steps (d) and (f), but does not occur in step (e).

21. A substantially pure antinuclear autoantibody that inhibits the growth of a tumor cell, wherein said autoantibody (a) is obtained from a non-immunized, healthy mammal, or from a hybridoma prepared with cells from a non-immunized, healthy mammal; and (b) binds specifically to (i) a surface of a living tumor cell and (ii) a protein released from a dead tumor cell or an antigen in the nucleus of said tumor cell, and (iii) does not bind to the surface of normal cells of said mammal.

22. An antinuclear autoantibody of claim 21, wherein said antinuclear autoantibody is obtained from an aged mammal.

23. An antinuclear autoantibody of claim 21, wherein said antinuclear autoantibody is obtained from a hybridoma prepared with cells from an aged mammal.

* * * * *